United States Patent
Dutta et al.

(10) Patent No.: US 9,997,260 B2
(45) Date of Patent: Jun. 12, 2018

(54) RETRIEVAL OF SIMILAR PATIENT CASES BASED ON DISEASE PROBABILITY VECTORS

(75) Inventors: Pradyumna Dutta, Bedford Corners, NY (US); Colleen M. Ennett, White Plains, NY (US)

(73) Assignee: Koninklijke Philips N.V., Eindhoven (NL)

( * ) Notice: Subject to any disclaimer, the term of this patent is extended or adjusted under 35 U.S.C. 154(b) by 1645 days.

(21) Appl. No.: 12/810,021

(22) PCT Filed: Dec. 8, 2008

(86) PCT No.: PCT/IB2008/055135
§ 371 (c)(1),
(2), (4) Date: Jul. 28, 2010

(87) PCT Pub. No.: WO2009/083833
PCT Pub. Date: Jul. 9, 2009

(65) Prior Publication Data
US 2010/0312798 A1    Dec. 9, 2010

Related U.S. Application Data

(60) Provisional application No. 61/017,323, filed on Dec. 28, 2007.

(51) Int. Cl.
*G06F 17/30* (2006.01)

(52) U.S. Cl.
CPC .................................. *G16H 50/70* (2018.01)

(58) Field of Classification Search
USPC .......................................................... 705/2–4
See application file for complete search history.

(56) References Cited

U.S. PATENT DOCUMENTS

| 6,108,635 | A  | * | 8/2000 | Herren et al. ..................... 705/2 |
| 6,177,940 | B1 | * | 1/2001 | Bond et al. ..................... 434/262 |
| 7,181,375 | B2 | * | 2/2007 | Rao et al. ......................... 703/2 |
| 7,457,731 | B2 | * | 11/2008 | Rao ................................. 703/2 |
| 2001/0020229 | A1 | * | 9/2001 | Lash ..................... B82Y 10/00 705/3 |
| 2003/0125988 | A1 | * | 7/2003 | Rao et al. ......................... 705/3 |

(Continued)

OTHER PUBLICATIONS

Feret, M. P., et al.; Combining Case-Based and Model-Based Reasoning for the Diagnosis of Complex Devices; 1997; Applied Intelligence; 7:57-78.

(Continued)

*Primary Examiner* — Mark Holcomb

(57) ABSTRACT

A method of retrieving similar patient cases from a medical database includes matching a current patient case against a plurality of clinical profiles resulting in a set of matching clinical profiles. The method further includes determining a degree of membership of the current patient case in each clinical profile from the set of matching clinical profiles based upon a degree of match between the current patient case and the clinical profile. For at least one clinical profile from the set of matching clinical profiles, the method includes retrieving those similar patient cases from the medical database that have a substantially corresponding degree of membership as the current patient case.

20 Claims, 4 Drawing Sheets

(56) References Cited

U.S. PATENT DOCUMENTS

| | | | |
|---|---|---|---|
| 2003/0191666 A1* | 10/2003 | Kline | G06F 17/18 705/2 |
| 2004/0117367 A1 | 6/2004 | Smith et al. | |
| 2006/0259329 A1* | 11/2006 | Kline | 705/3 |
| 2008/0126277 A1* | 5/2008 | Williams et al. | 706/14 |
| 2010/0312798 A1 | 12/2010 | Pradyumna et al. | |

OTHER PUBLICATIONS

Forgy, C.; Rete: a fast algorithm for the many pattern/many object pattern match problem; 1982; Artificial Intelligence; 19:17-37.

Frize, M., et al.; Clinical decision-support systems for intensive care units using case-based reasoning; 2000; Medical Engineering & Physics; 22:671-677.

Huang, M-J., et al.; Integrating data mining with case-based reasoning for chronic diseases prognosis and diagnosis; 2007; Expert Systems with Applications; 32:856-867.

Richter, M. M.; Introduction to Case-Based Reasoning Technology; 1998; Lecture Notes in Computer Science; vol. 1400:1-15.

Wilson, D., et al.; Case-Based Decision Support for Intelligent Patient Knowledge Management; 2006; IEEE Trans on Int'l. Conf. on Intelligent Systems; pp. 130-135.

Zadeh, L. A.; Fuzzy Sets; 1965; Information & Control; 8:338-353.

\* cited by examiner

RETRIEVAL OF SIMILAR PATIENT CASES BASED ON DISEASE PROBABILITY VECTORS

FIELD OF THE INVENTION

The invention relates to case matching and in particular, to a method of retrieving similar patient cases from a medical database. The invention relates further to a system of retrieving similar patient cases from a medical database. The invention relates further to a computer program product, comprising instructions which, when carried out by a computer, causes the computer to carry out such a method.

BACKGROUND OF THE INVENTION

Case matching, also known as similarity matching, has been used to provide inferences about solving a problem using evidence from past examples or cases. Case matching can be used to assist health-care providers by making a treatment recommendation using information from similar past patient cases. Historical patient data can assist care providers with predicting the outcomes of particular clinical interventions on a patient. Finding similar patients in a database is a time and resource intensive process. There is a trade-off between having a large enough database that increases the chances of finding similar patients and the amount of time taken to search a large database. The similarity matching algorithm, that finds patients similar to the currently treated patient, must respond quickly to be effective and not impose its own time requirements on the patient treatment process. In addition, the cases that are found must be evaluated with regard to their relevance to the current case. Medical classification systems exist, such as ICD-9 (International Classification of Diseases, version 9). ICD-9 codes are diagnosis codes that classify diseases, signs, symptoms, abnormal findings, complaints, social circumstances and external causes of injury or disease (ICD-9-CM, refers to the Clinical Modification extension designed to capture more morbidity data and the addition of procedure codes). These classification codes are assigned to the patient after being discharged from the clinical setting. Typically, these codes are used for morbidity and mortality statistics, and in the USA for reimbursement systems.

A problem with case matching is that it is very difficult of performing a matching between patients who have overlapping medical conditions.

BRIEF DESCRIPTION OF THE INVENTION

In one aspect of the invention, a method of retrieving similar patient cases from a medical database includes matching a current patient case against a plurality of clinical profiles resulting in a set of matching clinical profiles. For each clinical profile from the set of matching clinical profiles, the method further includes determining a degree of membership of the current patient case based upon a degree of match between the current patient case and the clinical profile. Based on the clinical profiles in the set of matching clinical profiles, similar patient cases are retrieved from the medical database that are identified as having a substantially corresponding degree of membership in at least one of the clinical profiles as the current patient case.

Using a degree of membership is based upon the insight that patients with overlapping conditions, i.e. with a corresponding degree of membership, are more similar and that it makes more sense to compare a patient with these similar patients. By the introduction of a degree of membership in a clinical profile, as described in Zadeh, L. A. *Fuzzy sets*. Information & Control 1965; 8:338-353, patients can be retrieved in terms of the degree to which they are similar in terms of any overlapping conditions. According to another aspect of the present application, the method comprises: matching the current patient case at multiple points in time against the plurality of clinical profiles resulting in a set of matching clinical profiles for each of the multiple points in time; and performing the step of determining and retrieving for each of the multiple points in time. With the introduction of multiple points in time for which a current patient is matched against a clinical profile, similar patient cases can be retrieved over time as well. It enables updating the set of matching clinical profiles and similar patient cases according to the progress of the current patient.

According to another aspect of the present application, each of the clinical profiles catalogs a medical condition according to at least one of the following patient data variables: conditional data, event-specific data, demographic data, clinical data, medical history, family history, social history, diagnosis history, and treatment history. The patient data may be condition-specific, like congestive heart failure, myocardial infarction, sepsis, as well as diseases such as coronary artery disease, lung cancer, cystic fibrosis, etc. or event-specific, like acute blood pressure drop, edema, high respiratory rate, low ejection fraction, chest pain, positive biopsy, etc. The independent specifications in a profile may include demographic data, like age, sex, height, weight, body mass index. The clinical profile specifications may include clinical data, like lab results, imaging tests, non-imaging tests, stress tests. It may further include history of present illness, like symptoms, signs, past medical history, like co-morbidities, family history, social history, like if smoker, alcohol intake, review of physiological systems, medications, allergies, physical exam, initial impression, differential diagnosis, and treatment plan data. By including at least one of these data into a clinical profile, similar patients can be retrieved based upon similar values of these data.

According to another aspect of the present application, each clinical profile is organized into a plurality of levels, where each level is further specified with a set of one or more specifications and associated variables, and the current patient case matches the clinical profile if the patient data and specification(s) of at least a first level are matched. The clinical profile consists of multiple levels of specifications for categorizing patient cases. The top level of specifications, involves specifications that must be true for the clinical profile to apply to the patient. Another level may involve specifications normally associated with the clinical profile but are not necessary specifications that must be true for the clinical profile to apply to the patient. This level may be used to indicate to a user missing data which can be overcome by ordering a specific test. For example: for a patient with risk factors or comorbidities associated with diabetes, the health care provider could be advised to order a glucose test.

According to another aspect of the present application, the method comprises retrieving information about treatment given to the similar patient cases from the medical database and presenting the information to a user. Such information may be presented to a user for example as raw data, or in the form of statistics. It allows a user to give more insight in the possible treatments and outcomes of similar patient cases in order to make a better decision about tests and treatments that may be ordered for the current patient.

In accordance with another aspect of the invention, a system for retrieving similar patient cases from a medical database includes a matcher which matches a current patient case against a plurality of clinical profiles resulting in a set of matching clinical profiles. A determiner determines a degree of membership of the current patient case in each clinical profile from the set of matching clinical profiles based upon the degree of match between the current patient case and the clinical profile. A retriever, based on the clinical profiles in the set of matching clinical profiles, retrieves similar patient cases from the medical database that are identified as having a substantially corresponding degree of membership in at least one of the matching clinical profiles as the current patient case.

In another aspect of the invention, a computer program includes instructions which, when carried out by a computer, cause the computer to carry out a method according to one aspect of the invention.

In another aspect of the invention, a method includes storing a set of clinical profiles in memory, at least some of the clinical profiles including a plurality of specifications. A set of prior patient cases is stored, the cases being indexed according to their membership in at least one of the stored clinical profiles. A current patient case for a patient is matched against the plurality of stored clinical profiles, the matching including comparing the specifications with the patient case to identify matching specifications. The method further includes identifying a specification for which one outcome of a test for the patient is able to establish a match with one of the specifications of a clinical profile for which there is already at least one matching specification and identifying the test to a user.

The advantages and effects which are achieved by the method, system and computer program product are described below.

BRIEF DESCRIPTION OF THE DRAWINGS

These and other aspects of the invention will be apparent from and elucidated with reference to the embodiments described hereinafter as illustrated by the following Figures.

DESCRIPTION OF EMBODIMENTS

Figure 1:
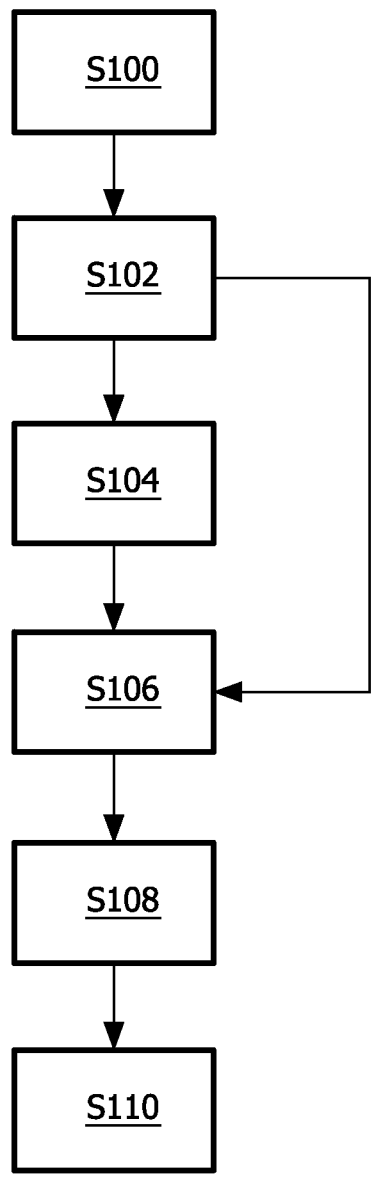
FIG. 1 illustrates the main steps of the method according to the invention.

A Clinical Profile (CP) catalogs a medical condition in terms of a set of specifications associated with that medical condition which may be evident in a patient having the medical condition. Each clinical profile is intended to capture correlations amongst patient variables for a specified presenting medical condition, e.g., sepsis. Such a CP generally includes a set of independent specifications based on variables such as demographic data (age, sex, height, weight, body mass index), clinical data (lab results, imaging tests, non-imaging tests, stress tests), and history and physical information from an admission report such as chief complaint (presentation), history of present illness (symptoms, signs), past medical history (comorbidities), family history, social history (if smoker, alcohol intake), review of physiological systems, medications, allergies, physical exam, initial impression, differential diagnosis, and treatment plan data, and the like which are known to be associated with that medical condition and any variables under which those specifications are considered to be satisfied for that medical condition. Each specification generally corresponds to data such as a test result, diagnosis, demographic data or measurement reading which may be acquired for a patient at an instant of time.

In a set of stored CPs, each CP may refer to a different medical condition or variation of a medical condition such that the specifications and/or their associated variables are different from one CP to another CP.

The CPs maybe linked to patient cases. Patient cases each comprise data for a specific patient. Advantageously, the data of a patient case may be medical data obtained from different tests or measurements on the patient by a physician or data obtained by the patient himself and may include data relating to one or more of the specifications in a given clinical profile against which the data can be matched.

Advantageously, the CP furthermore consists of multiple levels of specifications for categorizing patient cases, each level having one or more of the specifications associated with it. For example, there may be at least two levels, a first of the levels specifying any required specifications for the CP and one or more additional levels specifying specifications which may be evident in a patient having the medical condition, but which are not necessarily evident for the patient to be diagnosed with the medical condition. As an example, a CP may apply for a patient having Type 2 diabetes, and the levels may be "definitional level", "comorbidities level", and "risk factor level". The "definitional level" involves specifications that must be true for the CP to apply to the patient. The "comorbidities level" and "risk factors level" involves specifications normally associated with the CP but those that are not necessary specifications. In clinical terminology, a comorbidity is the presence of one or more disorders (or diseases) in addition to a primary disease or disorder. Comorbidities generally include other medical conditions which are often found in patients having the medical specification of that CP. Thus, for example, a patient having diabetes is also quite likely to suffer from nephropathy (a kidney disorder). The "risk factors level," enumerates the risk factors, if any, associated with the CP. Examples of risk factors for the diabetes CP include age, gender, diagnosis of the disease in either parent, etc. Advantageously, each level is associated with a weight (or multiple weights). The weight indicates the relative importance of a given level, with the highest weight generally being accorded to the definitional level. The assignment of the weights may e.g. be a manual operation performed by a clinical expert. As an example, a clinical profile CPn could be defined in the following way:

TABLE 1

| CPID | CP n |
|---|---|
| Medical condition | Diabetes |
| CP Definitional level: weight = 1.0 | HgbA1c >7% |
| CP Comorbidities level: weight = 0.6 | Retinopathy |
|  | Nephropathy |
| CP Risk factors level: weight = 0.3 | Heart disease |
|  | Gender |
|  | Age >60 |
|  | Race |

As shown in table 1, the left column shows the descriptions of the values in the right column. The clinical profile ID (CPID) identifies CPn (where n is a number, i.e., CP1 or CP234, etc.), the medical condition for CPn is Diabetes, and the subsequent rows are different levels having associated thereto the different weights. The right column also shows the different sets of specifications for each of the levels. Accordingly, the first (definitional) level has one (or more) specifications, here an amount of a particular serum protein, HgbA1c, which must be greater than 7% for the specification to be satisfied. This level is given the maximum weight 1.0 because this particular level is the most relevant for this particular Diabetes CP. On the other hand, for the last level relating to the Risk factors: heart disease condition, gender, age and race, which are considered less relevant; this level is assigned the associated weight of 0.3, i.e. less relevant. Accordingly, the levels are unequal in importance and this is expressed mathematically by using the weights. The weights presented in table 1 are for illustrative purposes only, and may differ for different CPs. Each specification in a given level may or may not have the same weight.

The different levels aid the detection of problems represented by the CP when particular tests have not been conducted. For instance, if a patient state indicates a match with the majority of comorbidities for diabetes but no blood sugar test has been done, a recommendation could be made to the health care provider to do a fasting glucose test. Not only does this allow improved diagnosis, it aids in defining the patient case more accurately for finding matches with the set of clinical profiles. A second application of the additional levels thus is to aid similarity matching.

Furthermore, the additional levels of specifications allow a determination of a "degree of membership" to a CP. In general, the larger the (weighted) number of comorbidities and risk factor specifications that are true for a given patient, the larger his or her degree of membership to that CP.

Advantageously, additional levels, in addition to definitional, co-morbidities and risk factors, are defined to aid inference for test recommendations, and for similarity matching, or to meet other requirements.

Optionally, a CP is further associated with metadata containing at least one of the following: an identifier identifying the ID of a particular patient who has been determined to be a member of that clinical profile, an identifier specifying the Clinical Profile Membership Set (CPMS), as described below, for the particular patient, a start time identifier identifying a start time of the particular CPMS, a start time identifier identifying a start time of the particular CPMS caused by a change in the patient's membership of one or more CPs, an end time identifier identifying an end time of a particular CPMS, and an end time identifier identifying an end time of a particular CPMS caused by a change in the membership of one or more CPs. This metadata allows for more details identifying the patient and/or the content of the CPs, and/or for determining when different interventions were started/ended etc.

The clinical profiles can be associated with a time stamp within the patient case to indicate the point in time when the clinical profile was relevant for the patient. This may be more closely tied to clinical events such as an acute blood pressure drop, but can also be related to disease-specific profiles that define how long a patient has had the disease.

Several different approaches may be used for developing clinical profiles, such as:
(1) Hypothesize the specifications, variables and ranges of their values, for the profile based on clinical knowledge. A physician expert, or a survey of literature, provides a list of specifications, variables and their ranges.
(2) Discover relevant variables that affect a particular outcome: this can be determined using data analysis techniques such as Principal Components Analysis, artificial neural networks, or others, on a database of prior patient cases.
(3) Do a guided discovery of clinical profiles by performing weighted searches of the database. Such a process could involve an interface that allows one to specify a clinical profile and search the database for patient case matches. The interface would allow selection of a subset of variables and allow the user to assign weights to convey their degree of importance in the clinical profile. The user would be able to save and retrieve previous clinical profiles. The interface would respond with immediate feedback on the number of patient cases in a database that match the suggested clinical profile.

FIG. 1 illustrates the main steps of a method of retrieving similar patient cases from a medical database according to the one aspect of the invention. Briefly, the method proceeds as follows. The method starts at S100. At S102, a current patient case is matched against a plurality of clinical profiles resulting in a set of matching clinical profiles. This step involves scanning the current patient's recent historical data in the patient case to find matches to the clinical profiles. Optionally, at S104, a representation of the match, such as a vector, is generated for each matching clinical profile. At S106, for each clinical profile from the set of matching clinical profiles, a degree of membership of the current patient case is determined, based upon a degree of match between the current patient case and the clinical profile. Steps S104-S106 are repeated for each of the clinical profiles to generate a membership set for the patient case. The membership set may include each of the CPs that the patient case is determined to have membership in (or at least a threshold degree of membership in). This membership set of one or more profiles, with varying degree of membership, for the current patient at the current time thus encapsulates the current patient's condition at the current time.

At S108, based on the CPs in the membership set, similar patient cases are matched and retrieved from the medical database. The patient cases retrieved may include some or all of the patient cases that are identified as having a substantially corresponding degree of membership in each of the CPs in the membership set as the current patient case. The similar patient cases are presented to the user through a user interface. The method ends at S110. Further details of these steps follow.

The method assumes that patient data for a current patient case has been stored in computer readable and/or processable form and that access is made available to stored CPs, the associated level weights, and a patient database storing prior patient cases comprising patient data, where each of the stored prior patient cases is associated with a degree of membership for at least some of the stored CPs.

Within S102, a current patient profile is matched against a plurality of clinical profiles as follows: A matching is performed between the patient's data and the various specifications for one or more of the levels of the CPs. The result of the matching is that one or more CPs is associated to the patient case where there is a match of the patient's data with the specifications for the definitional level and optionally one or more matches with one or more of the specifications at the other levels. As an example, if one portion of the patient's data matches one or more specifications in the set of specifications at the "comorbidities level" for a specific CP, then that CP is associated to the patient, if the patient also matches all of the specifications at the definitional level. Accordingly, the patient's data is "classified" into the levels of the specific CPs.

The result of the matching step S102 may e.g. be a vector A(patient)=[CP1,CP2,CP3,CP4, ... , CPN]), where each vector element is a CP for a certain medical condition. Since the CPs each have an associated dimension M representing the number of specifications in the CP (their dimensions may of course be different, M could be the largest dimension), the vector A(patient) could be represented by an N×M matrix, where M is the dimension of the CP and N the number of CPs. For simplicity, the term vector will be used to apply to any representation of the output of the match between the patient data and the set of CPs. Accordingly, CP1 can as an example have a single specification in a level in common with the patient's data (e.g. CP1 has the specification congestive heart failure at the Comorbidities level, and a portion of the patient's data specifies that the patient has congestive heart failure), CP2 has 10 levels representing specifications which may be evident within the patient's data, etc.

In one embodiment, the expression of A(patient) may show only those CPs that have specifications that are present in the patient's data. In another embodiment, the expression may be such that all the CPs are included in vector A even if some of the CPs, e.g. CP3 and CP4, have no specifications in common with the patient's data. Thus, the vector elements for this CP may be considered as empty, i.e. CP(patient)= [CP1, CP2, Ø, Ø, CP5, ... , Ø, CPN]. This means that the entire set of CPs is included in the vector, whether or not they match with the patient's data.

Within S104, the weights within a CP are optionally used for determining effective weighted values for each of the specifications of the patient's data matching specifications with the levels of the CPs. As an example, each element of the determined vector includes a set of weighted values, e.g., one weighted value for each of the specifications. The weighted values may be the product of the weight for the level and a value assigned to the specification based on the comparison with the patient data. The weights may be entered by a clinical expert that selects the weights based on the importance of the levels as discussed previously in table 1 and preferably presented in a declining order. e.g. CP1= [0.8, 0.4, 0.3, 0.15, 0.1, 0.1], CP2=[0.9, 0.5, 0.4, 0.35, 0.3, 0.2, 0.1] etc. As an example, assume that for a given patient the HgbA1c is not tested but there is existence of Nephropathy. The existence may be evaluated as true=1 or wrong=0. In this case, the fact that HgbA1c has not been tested may in terms of mathematical terminology be written as 0*1.0=0, where "0" means that it was not tested (or that there is no existence of HgbA1c) and 1.0 is the weight associated to the CP Definitional level. However, the fact that an existence of Nephropathy was detected in the patient's data gives the effective weighted value for the CP Comorbidities level 1*0.6=0.6, where "1" means simply that Nephropathy was detected, i.e. true=1, and "0.6" stands for the weighted value associated to the Comorbidities level (see table 1). Thus, the effective weighted value for the CP Definitional level is zero and the effective weighted value for CP Comorbidities level equals 0.6. Additionally, assuming that the patient's age is less than 60 years, the effective weighted value for the CP risk factors level would be 0*0.3=0, where the value is "0" because the patient is <60 years old, and "0.3" is the weight of the CP risk factors level (see table 1). The membership for this particular CPn may be represented as [0, 0.6, 0]. In this embodiment, a single weighted value is assigned to each level, which may be based on the weighted values for each of the specifications in that level. This is performed for all the CPs, i.e. CP1, ... , CP n, ... , CPN. Thus, a certain patient may have the following membership: [CP1:[0, 0, 0], CP2:[0, 0.8, 0.3], ... , CP n: [0, 0.6, 0], ... , CPN[0, 0, 0]].

Within S106, each respective CP having at least one specification or at least one level (generally, at least the specifications of the definitional level) matching with the patient's data is determined, resulting in a CP membership in accordance with a membership rule. Generally, the effective weighted values are used as input data. The calculation results in a CP membership value set for the patient for that CP to be used for determining a Clinical Profile Membership Set (CPMS) of membership values for the CPs.

Referring to the previous example, where the effective weighted values of CPn are [0, 0.6, 0], the CP membership may be determined based on various membership rules. One rule may e.g. be to select out the maximum value, i.e. max[0, 0.6, 0]=0.6, where 0.6 is the membership value for CPn. Another example of a membership rule is: sum[0, 0.6, 0]=0.6, i.e. summing up all the vector elements (which in this case is the same). Referring to the patient where CP1:[0, 0, 0], CP2:[0, 0.8, 0.3], CP3:[0, 0, 0], ... , CPn:[0, 0.6, 0], ... CPN-1[0.8, 0.2, 0],CPN[0, 0, 0]], table 2 shows how the CP membership set for this patient would look like if the membership rule is "max" rule:

TABLE 2

| CP | CP1 | CP2 | CP3 | ... | CPn | ... | CPN-1 | CPN |
|---|---|---|---|---|---|---|---|---|
| Membership value | 0 | 0.8 | 0 | | 0.6 | | 0.8 | 0 |

Table 3 shows how the CP membership set would be in case the membership rule is "sum" rule.

TABLE 3

| CP | CP1 | CP2 | CP3 | ... | CPn | ... | CPN-1 | CPN |
|---|---|---|---|---|---|---|---|---|
| Membership value | 0 | 1.1 | 0 | | 0.6 | | 1.0 | 0 |

The term "membership rule" may as an example include any kind of mathematical operation or mathematical rule. As an example, the membership rule may include selecting the largest element of the CP1, CP2, CP5 and CPN, or it could include calculating the sum in each of these CPs. Accordingly, by introducing this concept of membership or the degree of membership in a clinical profile, see Fuzzy Logic: "*Zadeh, L. A. Fuzzy sets. Information & Control* 1965; 8:338-353", depending upon the degree of match between patient data and the CP specifications, the data from the currently evaluated patient, preferably at an instant of time, is matched against all CPs. From this process a membership degree is provided in each CP for the patient, preferably at that time. The term membership can refer to any CP for which the assigned membership value, as determined by the membership rule, is non zero (or above a predetermined threshold). The membership set for the current patient in a given instant of time can be defined as the set of CPs with non-zero (above threshold) membership values. The degree of membership in a CP can be a function of the membership value, with higher values generally being associated with higher membership degrees. The membership degree can be the membership value, a ranking based on all the membership values, or the like. The membership set concept allows matching patients in terms of the degree to which they are similar in terms of any overlapping specifications. In this way a CP database is constructed for a patient case that allows for similar patient cases to be selected from a medical database.

Within S108, case matching is performed between the current patient case and the medical CP database by comparing the CPMS of the current patient case and the CPMSs of prior cases. In one embodiment, cases with similar degrees of membership in the CPs are retrieved.

By associating the CPs with a "time stamp" in the patient case, it is possible to indicate the point in time when the CP was relevant for the patient. As such, the present invention allows for continuously updating the set of matching CPs and thus matching similar patient cases. This can be done by propagating the changed values through CP definitions, such as performed by the Rete algorithm for propagating inferences from a large number of facts through a production rule system, "*Forgy, C. Rete: a fast algorithm for the many pattern/many object pattern match problem. Artificial Intelligence* 1982; 19:17-37". Including a time indicator may be more closely tied to clinical events such as an acute blood pressure drop, but can also be related to disease-specific profiles that define how long a patient has had the disease.

Within S108 those similar patient cases from the medical database are retrieved for each CP from the set of matching CPs, that have a substantially corresponding degree of membership as the current patient case. If an exact match with the same clinical profiles is not found, similarity metrics that define a degree of match with the membership set for the current patient may be employed. For example, if multiple patients appear similar, additional measures such as k-nearest neighbors, or other similarity measures as are well known in the art, could be applied to determine further degrees of similarity.

Optionally within S108, the similar patient cases are presented to the user through a user interface. The presentation includes all patient data of the patient cases. Alternatively, a subset of the patient data is presented. Information on interventions and outcomes based on the similar cases is presented to the health-care provider. For example, the presentation may include the different treatments of the similar patient cases. Based upon the presented information, a clinician can decide upon which treatments and studies need to be performed for the current patient.

Further within S108, optionally the CP (or CPs) which caused the similar patient case to be retrieved is also identified to the user, allowing the user to evaluate whether the medical condition associated with that CP is clinically reasonable and to identify other tests whose outcome may impact the determined degree of membership in that CP.

The exemplary method overcomes several problems with existing methods. Prior methods often require the user to provide a finding or diagnosis before a patient can be classified with a medical condition. The exemplary method provides automatic classification (e.g., degree of CP membership) and does not require the user to assign a diagnosis of the patient's current condition. The method then performs a search of the database of patient cases based on the classification. The method also overcomes the difficulty of matching patients who have overlapping medical conditions. The exemplary method scales to match multiple overlapping conditions by generating a membership set. The method also overcomes the problem of spurious correlations in matched cases. A common problem in performing automated searches or matching is that the matched cases are based on spurious correlations. The method ensures that the matches are based on clinically valid reasoning by considering multiple specifications for each CP.

Another advantage of the exemplary method is that faster database searches may be achieved. A common problem in searching large databases is the trade-off between exhaustiveness of the search, and the time taken for the search. The exemplary CPs enable an a priori cataloguing of the patients in the database to facilitate faster case matching in real-time decision support. In the exemplary method, membership sets are used as an indexing scheme. Using CP membership sets as a search index may facilitate faster searches and retrievals as the number of variables searched is reduced by an order of magnitude (from patient variables to CPs).

The method illustrated in FIG. 1 may be implemented in a computer program product that may be executed on a computer. The computer program product may be a tangible computer-readable recording medium on which a control program is recorded, such as a disk, hard drive, or may be a transmittable carrier wave in which the control program is embodied as a data signal. Common forms of computer-readable media include, for example, floppy disks, flexible disks, hard disks, magnetic tape, or any other magnetic storage medium, CD-ROM, DVD, or any other optical medium, a RAM, a PROM, an EPROM, a FLASH-EPROM, or other memory chip or cartridge, transmission media, such as acoustic or light waves, such as those generated during radio wave and infrared data communications, and the like, or any other medium from which a computer can read and use.

Figure 2:
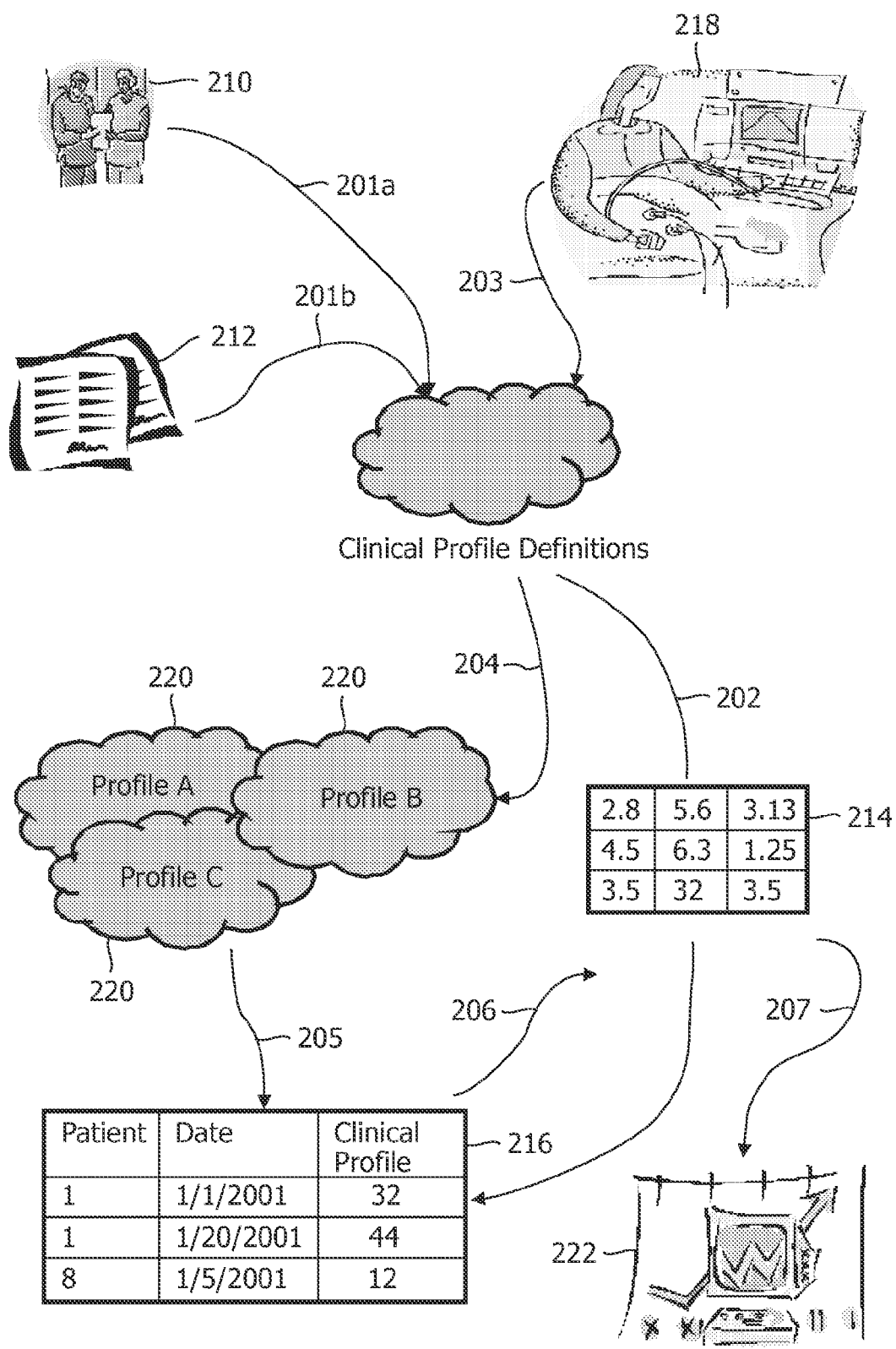
FIG. 2 describes matching a current patient case against clinical profiles in a schematic way.

FIG. 2 describes matching a current patient against clinical profiles in a schematic way. Reference numerals 201a and 201b refer to the development of a clinical profiles database that can quickly find patients similar to the current one under treatment, where a set of clinical profiles is created that cover medical conditions of interest, where these clinical profiles apply to a set of retrospective patient data in a medical database prior to implementing similarity matching or a similarity matching algorithm. These clinical profiles cover a range of conditions of interest, and are derived from sources of medical knowledge, such as clinical studies 212 and expert physician opinion 210. Reference numeral 202 refers to the application of clinical profiles to the patient database 214 to verify that patients with the conditions defined in the profiles exist in the database. A clinical profile database 216 is created that indexes patient cases of clinical profiles that exist in the patient database. Each entry into the clinical profile database may consist of the following fields: Patient ID, Time, Clinical profile ID, and Degree of membership in clinical profile. Each record in the clinical profile database identifies when a clinical profile occurs for a given patient (i.e., when at least the definitional specification(s) are met). A patient case may belong to more than one clinical profile and each instance is listed in the clinical profile database. The clinical profiles of each patient will be determined with respect to all the presenting problems for the patient.

Reference numeral 203 refers to using a decision support system in real-time, where it is necessary to identify possible clinical profiles to which the current patient 218 may belong based on the presenting problems and relevant variables. The current patient data is applied to the CPs, as discussed previously. Reference numeral 204 refers to identifying a set of one or more CPs 220, with varying degrees of membership, for the current patient at the current time. This set that encapsulates the current patient's condition is termed a "clinical profile membership set" for the current patient at the current time. This process involves e.g. scanning the current patient's recent historical data to find matches to the clinical profiles. Reference numeral 205 depicts the step where the current patient's 218 clinical profiles 220 are used to search the clinical profile database 216 for similar patients (patients matching the same clinical profiles). If an exact match with the same clinical profiles is not found, other similarity metrics may be implemented that define a degree of match with the membership set for the current patient. Reference numeral 206 depicts the step where patient IDs of those in the clinical profile database that have a matching CP membership set are retrieved from the medical database 214. This approach using CPs thus functions as a method for similarity matching, as patients with medical conditions represented by the CPs are matched and retrieved from the medical database. If several matching patients are retrieved, then additional techniques such as k-nearest neighbors may be employed. Reference numeral 207 refers to presenting information on interventions and outcomes based on the similar cases to the health-care provider 222. The clinical profile(s) used to match the current patient to the patients in the medical database can be displayed at the output as evidence to show the variables that were used for matching using the similarity matching algorithm.

Figure 3:
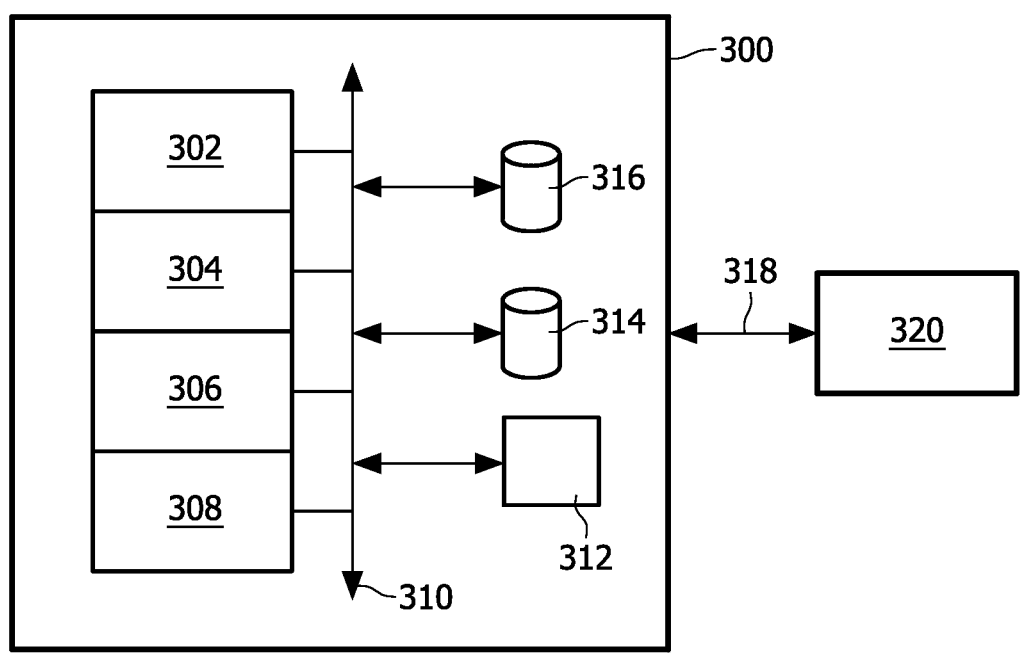
FIG. 3 schematically illustrates a system according to the invention.

FIG. 3 describes a system according to the invention in a schematic way. The system 300 comprises memories 302, 304, 306, and optionally 308 designed to comprise instructions which, when carried out by a processor 312 causes the system 300 to carry out the method according to the invention. The system further comprises a patient database 316, and a clinical profile database 314. The memories, processor, and databases are connected to each other through communication software bus 310. The system 300 is connected through an output/input interface 318 to a display 320. The memory 302 ("matcher") is designed to comprise instructions for carrying out matching a current patient case against a plurality of clinical profiles resulting in a set of matching clinical profiles. The memory 304 ("determiner") is designed to comprise instructions for carrying out determining a degree of membership of the current patient case in each clinical profile from the set of matching clinical profiles based upon the degree of match between the current patient case and the clinical profile. The memory 306 ("retriever") is designed to comprise instructions for carrying out retrieving for each clinical profile from the set of matching clinical profiles, those similar patient cases from the medical database that have a substantially corresponding degree of membership as the current patient case. Optionally the instructions of memory 304 and 306 comprise determining their respective functionality for multiple points in time. The memory 308 (which may be part of matcher 302) is designed to comprise instructions for carrying out matching the current patient case at multiple points in time against the plurality of clinical profiles resulting in a set of matching clinical profiles for each of the multiple points in time. The patient database 316 comprises patient data (prior cases) as previously described. Patient data for the current case may be stored in this or a separate memory during processing. The clinical profile database 312 comprises clinical profiles as previously described. The display 320 or other user input device allows for user interaction with the system, by enabling a user to provide input to the system and displaying the output of the system to the user. The output comprises feedback of information about the current patient and matching patients as previously described. The whole system may have a distributed nature in which for example the databases are located at a different geographical position then the memories, software bus and the processor. In this case the different parts of the system can communicate with each other making use of well known wired or wireless communication protocols.

Figure 4:
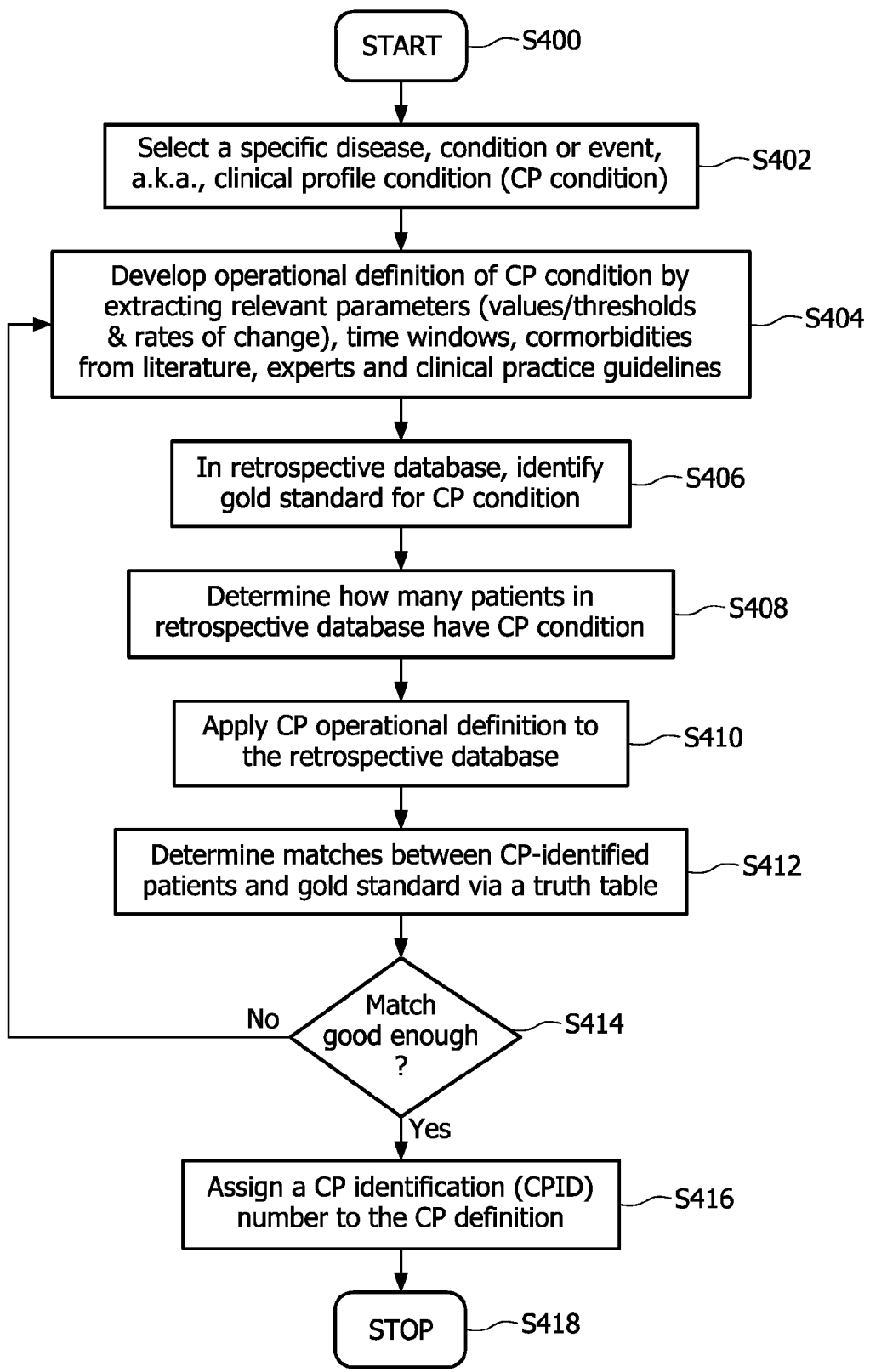
FIG. 4 illustrates an exemplary method for generating the clinical profiles.

FIG. 4 illustrates an exemplary method for generating the clinical profiles. The method begins at S400. S402 includes selecting a specific disease, condition or event, which is to be the clinical profile's medical condition (CP medical condition). S404 includes developing an operational definition of the CP medical condition by extracting relevant parameters (values/thresholds & rates of change), time windows, cormorbidities from literature, experts and clinical practice guidelines. S406 includes, using a medical database (e.g., database 316) to identify a gold standard for the CP medical condition. S408 includes determining how many patients in the medical database have the CP medical condition. S410 includes applying the CP operational definition to the medical database. S412 includes determining matches between CP identified patients and the gold standard via a truth table. At S414, an assessment is made as to whether the match good enough. If YES, at S416, a CP identification (CPID) number is assigned to the CP definition. If NO, the method returns to S404 where the operational definition is refined. The method ends at S418.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements, and by means of a suitably programmed computer. In the system claims enumerating several means, several of these means can be embodied by one and the same item of computer readable software or hardware. The mere fact that certain measures are recited in mutually different dependent claims does not indicate that a combination of these measures cannot be used to advantage.

The invention claimed is:

1. A method of retrieving similar patient cases from a medical database, the method comprising:
   storing, by the medical database, a plurality of clinical profiles, each clinical profile defined by a different medical condition and including a plurality of specifications associated with the medical condition, wherein each specification is associated with a weight, the weight indicating an importance of the specification to a diagnosis of the medical condition, wherein each clinical profile is divided into a plurality of levels with a set of the specifications within each level, wherein the specifications include comorbidities;
   storing, by the medical database, a plurality of patient cases comprising patient data, the patient data corresponding to one or more specifications;
   defining for each clinical profile, by a processor, membership rules defining degrees of membership in the clinical profile, wherein membership in the clinical profile is determined by a cumulative presence of one or more weighted specifications comprised in the clinical profile;
   indexing, by the processor, each patient case in the medical database as having a degree of membership in one or more clinical profiles based on the membership rules;

receiving, by the processor, a current patient case comprising current patient data;

searching, by the processor, the medical database comprising the plurality of clinical profiles and the plurality of patient cases;

matching, by the processor, the current patient case against the plurality of clinical profiles resulting in a set of matching clinical profiles, wherein the matching includes comparing the patient data for the current patient case with the specifications to determine whether there is a match for any of the specifications;

determining, by the processor, for each clinical profile from the set of matching clinical profiles, the degree of membership of the current patient case based upon the membership rules; and retrieving, by the processor, based on the clinical profiles in the set of matching clinical profiles, similar patient cases from the medical database that are identified as having a substantially corresponding degree of membership in at least one of the clinical profiles as the current patient case.

2. The method according to claim 1, wherein the matching comprises:

matching the current patient case at multiple points in time against the plurality of clinical profiles resulting in a set of matching clinical profiles for each of the multiple points in time;

and performing the step of determining and retrieving for each of the multiple points in time.

3. The method of claim 1, wherein the retrieving includes retrieving patient cases that are identified as having a substantially corresponding degree of membership in each of the clinical profiles of a membership set of the matching clinical profiles as the current patient case.

4. The method according to claim 1, wherein each of the clinical profiles catalogs a medical condition according to at least one of the following patient data variables: conditional data, event-specific data, demographic data, clinical data, medical history, family history, social history, diagnosis history, and treatment history.

5. The method according to claim 1, wherein the current patient case matches the clinical profile if all the specifications of at least a definitional one of the levels are matched with the patient data.

6. The method according to claim 1, wherein each of the levels is associated with a weight and wherein the degree of membership is based on at least one matching specification and its associated weight.

7. The method according to claim 1, wherein the degree of membership for a clinical profile is based on a number of the specifications that match the patient data.

8. The method of claim 1, further comprising, identifying a test to be performed on the patient whose outcome is one of the specifications of a clinical profile which has at least one other specification which matches the patient data.

9. The method according to claim 1, further comprising retrieving information about treatment given a patient in at least one of the similar patient cases from the medical database and presenting the information to a user.

10. The method of claim 1, further comprising, for one of the retrieved similar patient cases from the medical database, identifying for a user the clinical profile which was used to retrieve the similar patient case.

11. The method of claim 1, further comprising linking the current patient case to at least one clinical profile from the set of matching profiles.

12. The method of claim 11, further comprising linking the current patient case to a membership set of the set of matching profiles based on the degree of membership.

13. The method of claim 11, further comprising time stamping the current patient case based on a time at which the current patient case is linked to the at least one clinical profile from the set of matching profiles.

14. A system for retrieving similar patient cases from a medical database, the system comprising a memory storing a set of instruction and a processor, wherein the processor executes the set of instructions to implement:

a searcher which searches the medical database comprising a plurality of clinical profiles and a plurality of patient cases, wherein each clinical profile is defined by a different medical condition and includes a plurality of specifications associated with the medical condition, wherein each specification is associated with a weight, the weight indicating an importance of the specification to a diagnosis of the medical condition, wherein each clinical profile is divided into a plurality of levels with a set of the specifications within each level, wherein the specifications include comorbidities, wherein each patient case comprises patient data, the patient data corresponding to one or more specifications, wherein each clinical profile defines membership rules, the membership rules defining degrees of membership in the clinical profile, wherein membership in the clinical profile is determined by a cumulative presence of one or more weighted specifications comprised in the clinical profile, wherein each patient case is indexed in the database as having a degree of membership in one or more clinical profiles based on the membership rules;

a matcher which matches a current patient case comprising current patient data against the plurality of clinical profiles resulting in a set of matching clinical profiles, wherein the matcher compares the patient data for the current patient case with the specifications to determine whether there is a match for any of the specifications;

a determiner which determines the degree of membership of the current patient case in each clinical profile from the set of matching clinical profiles based upon the membership rules;

and a retriever which, based on the clinical profiles in the set of matching clinical profiles, retrieves similar patient cases from the medical database that are identified as having a substantially corresponding degree of membership in at least one of the matching clinical profiles as the current patient case.

15. The system according to claim 14, wherein the matcher is designed for matching the current patient case at multiple points in time against the plurality of clinical profiles resulting in a set of matching clinical profiles for each of the multiple points in time;

and the determiner and retriever are designed for determining and retrieving for each of the multiple points in time.

16. The system of claim 14, further comprising memory which stores the plurality of clinical profiles.

17. The system according to claim 14, wherein each of the clinical profiles catalogs a medical condition according to at least one of the following patient data:

conditional data, event-specific data, demographic data, clinical data, medical history, family history, social history, diagnosis history, and treatment history.

18. The system according to claim 14, wherein the matcher determines a match between the current patient case and a clinical profile when all specifications of at least one level are matched with the patient data.

19. The system according to claim 18, further comprising an information retriever designed for retrieving information about treatment given to the similar patient cases from the medical database and a presenter designed for presenting the information to a user.

20. A computer program product embodied on a non-transitory computer readable medium comprising instructions which, when carried out by a computer, cause the computer to carry out the method, comprising:
   storing a plurality of clinical profiles in a medical database, each clinical profile defined by a different medical condition and including a plurality of specifications associated with the medical condition, wherein each specification is associated with a weight, the weight indicating an importance of the specification to a diagnosis of the medical condition, wherein each clinical profile is divided into a plurality of levels with a set of the specifications within each level, wherein the specifications include comorbidities;
   storing a plurality of patient cases comprising patient data in the medical database, the patient data corresponding to one or more specifications;
   defining, for each clinical profile, membership rules defining degrees of membership in the clinical profile, wherein membership in the clinical profile is determined by a cumulative presence of one or more weighted specifications comprised in the clinical profile;
   indexing each patient case in the medical database as having a degree of membership in one or more clinical profiles based on the membership rules;
   receiving a current patient case comprising current patient data;
   searching the medical database comprising the plurality of clinical profiles and the plurality of patient cases;
   matching the current patient case against the plurality of clinical profiles resulting in a set of matching clinical profiles wherein the matching includes comparing the patient data for the current patient case with the specifications to determine whether there is a match for any of the specifications;
   for each clinical profile from the set of matching clinical profiles, determining the degree of membership of the current patient case based upon the membership rules;
   and based on the clinical profiles in the set of matching clinical profiles, retrieving similar patient cases from the medical database that are identified as having a substantially corresponding degree of membership in at least one of the clinical profiles as the current patient case.

* * * * *